United States Patent
Zhang

(10) Patent No.: US 9,340,815 B2
(45) Date of Patent: May 17, 2016

(54) SPONTANEOUSLY IMMORTALIZED AVIAN CELL LINE

(71) Applicant: The United States of America, as represented by the Secretary of Agriculture, Washington, DC (US)

(72) Inventor: Huanmin Zhang, Okemos, MI (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 62 days.

(21) Appl. No.: 14/495,587

(22) Filed: Sep. 24, 2014

(65) Prior Publication Data

US 2015/0087022 A1    Mar. 26, 2015

Related U.S. Application Data

(60) Provisional application No. 61/881,522, filed on Sep. 24, 2013.

(51) Int. Cl.
C12N 5/077 (2010.01)
C12P 21/00 (2006.01)

(52) U.S. Cl.
CPC ............... C12P 21/00 (2013.01); C12N 5/0656 (2013.01); C12N 2710/16351 (2013.01); C12N 2740/11051 (2013.01)

(58) Field of Classification Search
None
See application file for complete search history.

(56) References Cited

PUBLICATIONS

Zhang, H., L.D. Bacon, and A.M. Fadly, "Development of an Endogenous Virus-Free Line of Chickens Susceptible to All Subgroups of Avian Leukosis Virus," Avian Diseases (2008) 52:412-418.

*Primary Examiner* — Addison D Ault
(74) *Attorney, Agent, or Firm* — John D. Fado; Gail E. Poulos

(57) ABSTRACT

Embodiments of the present invention relate to a spontaneously immortalized avian cell line, designated ZS-1. Immortalized avian cell line, ZS-1 is derived from primary chicken embryo fibroblasts (CEF). The ZS-1 cell line is free of endogenous retroviruses, including Avian Leukosis Viruses (ALV), and particularly ALV sub-group E. Moreover, the ZS-1 cell line susceptible to all subgroups of ALV, including subgroup E. Cells of the ZS-1 cell line and sub-clones thereof may be used for inter alia the production of viral agents, including recombinant viral agents, expression of recombinant proteins, and diagnostic assays.

9 Claims, No Drawings

SPONTANEOUSLY IMMORTALIZED AVIAN CELL LINE

REFERENCE TO RELATED APPLICATIONS

This application claims priority to U.S. Provisional patent Application U.S. Ser. No. 61/881,522, filed on Sep. 24, 2013, which is incorporated herein by reference in its entirety.

FIELD OF THE INVENTION

The invention relates to a spontaneously immortalized avian cell line derived from the primary chicken embryonic fibroblasts, and its use for production of viral agents, expression of recombinant proteins, laboratory tests for diagnostic purposes, etc.

BACKGROUND OF THE INVENTION

Avian leukosis virus (ALV) infections and expression are detrimental to the poultry industry (see e.g., Crittenden. (1991) Crit. Rev. Poult. Biol. 3:73-109. 1991; Goosen and de Boer (1983) Tijdschr. Diergeneeskd. 108:855-863; Payne (1998) Poult. Sci. 77:1204-1212; Zavala and Cheng (2006) Avian Dis. 50:209-215). There are five well-defined exogenous subgroups (A, B, C, D, and J) of ALV, which are associated with malignant neoplasms in chickens (see e.g., Crittenden. supra; Fadly et al. (2006) Avian Dis. 50:380-385; Fadly and Smith (1999) Avian Dis. 43:391-400; Fenton et al. (2005) Avian Pathol. 34:48-54; Lupiani et al. (2006) Avian Dis. 50:572-578; Meyers and Qualtiere (1977) J. Immunol. 118:1541-1548; Neiman et al. (1980) J. Virol. 34:178-186; Payne. supra; Payne et al. (1992) J. J. Gen. Virol. 73(11): 2995-2997; Prukova et al. (2007) Avian Pathol. 36:15-27; Witter and Crittenden (1979) Int. J. Cancer 23:673-678; Zavala et al. (2006) Avian Dis. 50:201-208).

Numerous subgroup E endogenous viruses are present in the genome of most chickens (see e.g., Aggrey et al. (1998) Br. Poult. Sci. 39:39-41; Astrin. (1978) Proc. Natl. Acad. Sci. U.S.A 75:5941-5945; Astrin et al. (1980) Cold Spring Harb. Symp. Quant. Biol. 44(2):1105-1109; Bacon et al. (2004) Avian Pathol. 33:233-243; Bacon et al. (2000) Poult. Sci. 79:1082-1093; Benkel. (1998) Poult. Sci. 77:1027-1035; Boulliou et al. (1992) Poult. Sci. 71:38-46; Crittenden and Motta. (1975) Virology 67:327-334; Crittenden et al. (1974) Virology. 57:128-138; Gorbovitskaia et al. (1998) Poult. Sci. 77:605-614; Grunder et al. (1995) Poult. Sci. 74:1506-1514; Ignjatovic (1988) J. Gen. Virol. 69(3):641-649; Rovigatti and Astrin. (1983) Curr. Top. Microbiol. Immunol. 103:1-21; Tixier-Boichard et al. (1997) Poult. Sci. 76:733-742). The presence of endogenous virus in tissue culture cells can lead to contamination of vaccines (see e.g., Fadly et al. supra; Johnson and Heneine (2001) J. Virol. 75:3605-3612; Witter and Crittenden. supra) and to emergence of new recombinant viruses between exogenous and endogenous viruses (see e.g., Benson et al. The unique envelope gene of the subgroup J avian leukosis virus derives from ev/J proviruses, a novel family of avian endogenous viruses. J. Virol. 72:10157-10164. 1998; Smith et al. Novel endogenous retroviral sequences in the chicken genome closely related to HPRS-103 (subgroup J) avian leukosis virus. J. Gen. Virol. 80(Pt 1):261-268. 1999].

Cellular resistance/susceptibility to exogenous and endogenous ALV is specifically determined by autosomal tumor virus (TV) loci, namely TVA, TVB, TVC, and TVJ, which carry alleles either encoding receptors mediating a specific subgroup of viral entry or blocking an entry.

TVA encodes a membrane protein related to the family of low density lipoprotein receptors (see e.g., Bates et al. (1993) Cell 74:1043-1051; Elleder et al. (2004) J. Virol. 78:13489-13500; Young and He (1993) J. Virol. 67:1811-1816) and is mapped to chicken autosomal chromosome 28 (see e.g., Schmid et al. (2000) Cytogenet. Cell Genet. 90:169-218).

TVB is the most complex TV locus, and is related to the tumor necrosis factor (see e.g., Brojatsch et al. (1996) Cell 87:845-855). There are three TVB alleles, TVB*S1, TVB*S3, and TVB*R. TVB*S1 codes for susceptible receptors mediating infection by ALV subgroups B, D, and E and is dominant to both TVB*S3 and TVB*R; TVB*S3 codes susceptible receptors for infection by subgroups B and D and is dominant to TVB*R; TVB*R encodes a truncated receptor, which permits neither B, D, nor E subgroups of ALV infection (see e.g., Adkins et al. (2001) J. Virol. 75:3520-3526; Zhang et al. (2007) Avian Pathol. 36:283-291). TVB is cloned (see e.g Adkins et al. (2000) J. Virol. 74:3572-3578; Brojatsch et al. supra; Klucking et al. (2002) J. Virol. 76:7918-7921) and mapped to the chromosome 22 (see e.g., Smith and Cheng. (1998) Microb. Comp. Genomics 3:13-20).

TVC encodes a protein most closely related to immunoglobin family. TVC is cloned and mapped to chicken chromosome 28, close to the TVA locus (see e.g., Dren and Pani. (1977) J. Gen. Virol. 35:13-23; Elleder et al. (2005) J. Virol. 79:10408-10419).

TVJ is the latest identified locus and reported as the chicken Na+/H+ exchanger type 1 (chNHE1) gene. TVJ encodes a 90 kDa cell surface protein and is mapped to chromosome 23 (see e.g., Chai and Bates. (2006) Proc. Natl. Acad. Sci. U.S.A 103:5531-5536. 2006).

Avian leukosis viruses are retroviruses. Retroviruses have a tendency to integrate into the germ line and are transmitted vertically thereafter to subsequent generations as endogenous retroviral sequences (see e.g., Coffin et al. (1997) Retroviruses. Cold Spring Harbor Laboratory Press, New York; Crittenden. supra). There are reportedly more than 20 known subgroup E endogenous virus (ev) genes in the chicken, which encode for endogenous viruses or their components. Such genes are present in virtually all chicken genomes (see e.g., Rovigatti and Astrin. supra; Smith. (1986) *Endogenous avian leukosis viruses*. In: Avian leukosis. de Boer, ed. Martinus Nijhoff Publishing, Boston. pp. 101-120; Tereba and Astrin (1980). J. Virol. 35:888-894).

The nonessentiality of endogenous viruses for the chicken was first demonstrated by the identification of a fertile Leghorn rooster that lacked ev genes (see e.g., Astrin et al. (1979) Nature 282:339-341). This was supported by identification of similar chickens (see e.g., Chernov et al. (1984) Folia Biol. (Praha) 30:342-348), and at least two lines have been developed free of ev genes (Bacon. (2002) The National Registry of Genetically Unique Animal Populations: USDA-ADOL chicken genetic lines. Natl. Anim. Germplasm Program, East Lansing, Mich.; Crittenden. (1991) supra; Gavora et al. (1989) J. Anim. Breed. Genet. 106:217-224). However, White Leghorn chickens that are free of ev genes are extremely rare (see e.g., Gavora et al. supra), and with the exception of line 0, lines do not exist that have been characterized for susceptibility or resistance to specific subgroups of ALV.

Line 0 was the first developed chicken line characterized as free of subgroup E endogenous viruses, with resistance to subgroup E (C/E; TVB*S3/*S3), and is maintained specific pathogen free. Line 0 has been available to the research community since the 1980s (see e.g., Bacon. 2002. supra; Bacon et al. 2000. supra; Crittenden et al. (1984) Avian Dis. 28:1037-1056). Line 0 has been essential for detection of exogenous viruses in tissue samples from chickens and for eradicating exogenous ALV from breeder flocks following critical infections with ALV A in egg layers (see e.g., Crittenden et al. (1984) supra; Holmen et al. (1999) J. Virol. 73:10051-10060) and ALV J in broilers (Fadly and Smith. supra). Line 0 is also the source for a widely used immortalized cell line known as the UMNSAH-DF-1 cell line (see e.g., Maas et al. (2006) Biologicals. 34:177-181).

The UMNSAH-DF-1 cell line (also referred to as simply DF-1 and deposited under accession number ATCC CRL-12203) was the first line of spontaneously immortalized avian cells (Foster et al. U.S. Pat. No. 5,672,485). DF-1 was derived from the chicken embryo fibroblasts of line 0, and has been claimed as the world's only retroviral negative spontaneously immortalized avian cell line. Df-1 has been widely used in varied research and diagnostic tests since it became commercially available.

However, despite these and other advances, the need remains for improved spontaneously immortalized cell lines which are free of retroviruses, including ALV.

Fortunately, as will be clear from the following disclosure, the present invention provides for these and other needs.

SUMMARY OF THE INVENTION

One embodiment of the present disclosure provides an immortal cell line ZS-1 derived from primary Chicken Embryo Fibroblasts (CEF) from the virus free chicken line, 0.TVB*S1, wherein the immortal cell line ZS-1 is free of avian leukosis virus (ALV) and supports virus replication. In one exemplary embodiment, the immortal cell line ZS-1, strain PTA-121623, derived from primary Chicken Embryo Fibroblasts (CEF) from the virus free chicken line, 0.TVB*S1 was deposited with the American Type Culture Collection (ATCC), Patent Depository, 10801 University Blvd., Manassas, Va. 20110, U.S.A. on Sep. 24, 2014.

Further, the subject deposit will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the strain. The depositor acknowledges the duty to replace the deposits should the depository be unable to furnish a sample when requested, due to the condition of the deposits. All restrictions on the availability to the public of the subject deposit will be irrevocably removed upon the granting of a patent disclosing it.

In another exemplary embodiment, the disclosure provides a cell culture or sub-clone of the immortal cell line ZS-1. In one exemplary embodiment, the cells comprising the cell culture are transformed with a heterologous nucleic acid construct operably linked to one or more expression control sequences.

In another exemplary embodiment, the disclosure provides a method for growing a virus comprising: (i) inoculating cells of a cell culture or sub-clone of immortal cell line ZS-1 derived from primary Chicken Embryo Fibroblasts (CEF) from the virus free chicken line, 0.TVB*S1, wherein the immortal cell line ZS-1 is free of avian leukosis virus (ALV) and supports virus replication, with a virus; (ii) allowing the virus to replicate in the cells of the immortal cell line ZS-1 thereby producing replicated virus; and (iii) recovering the replicated virus. In one exemplary embodiment the virus is a retrovirus. In another exemplary embodiment the retrovirus is an Avian Leukosis Virus. In still another exemplary embodiment, the Avian Leukosis Virus is an Avian Leukosis Virus subgroup E. In one exemplary embodiment, the method is used to test for the presence of viruses. In this embodiment, the method comprises inoculating the cell culture or sub-clone of immortal cell line ZS-1 in step (i) with a test sample.

In another exemplary embodiment, the disclosure provides method for producing recombinant protein comprising: (i) transforming cells of the immortal cell line ZS-1 with an expression vector comprising a nucleic acid sequence that encodes the recombinant protein operatively linked to a promoter effective for expression in the immortal cell line ZS-1, thereby providing transformed cells; (ii) allowing the transformed cells to express the recombinant protein; and (iii) recovering the recombinant protein from the transformed cells Other features, objects and advantages of the invention will be apparent from the detailed description which follows.

DETAILED DESCRIPTION OF THE INVENTION

Definitions

All technical and scientific terms used herein, unless otherwise defined below, are intended to have the same meaning as commonly understood by one of ordinary skill in the art; references to techniques employed herein are intended to refer to the techniques as commonly understood in the art, including variations on those techniques or substitutions of equivalent techniques which would be apparent to one of skill in the art. In order to more clearly and concisely describe the subject matter disclosed herein, the following definitions are provided for certain terms which are used in the specification and appended claims.

The term "immortalization" as used herein, refers to cells capable of growing in culture for greater than 30 passages that maintain a doubling time in culture of about 1 to about 2 days and have been in continuous culture for greater than about 6 months. Avian cells are generally considered immortalized after about 20 to about 25 passages in culture. Immortalized cells are differentiated from immortalized cell lines also known as transformed cells e.g., HeLa cells, in that unlike transformed cells, immortalized cells are density dependent and/or growth arrested (e.g., contact inhibited). Immortalized cell lines also known as transformed cells are capable of growth in soft agar and are usually able to form tumors when injected into laboratory animals.

The term "transform with a nucleic acid" or "transformed with a nucleic acid" as used herein refers to cell(s) produced by introducing into the cell(s) an exogenous nucleic acid or nucleic acid analog which replicates within that cell, that encodes a polypeptide sequence which is expressed in that cell, and/or that is integrated into the genome of that cell so as to affect the expression of a genetic locus. Typically, transformation is achieved by any of the standard methods referred to in the art as transformation, transfection, transduction, electroporation, ballistic injection, and the like. The method of transformation is chosen to be suitable to the type of cells being transformed and the nature of the genetic construct being introduced into the cells. Exemplary transformation methods include e.g., those described generally in, e.g., Sambrook et al. (1989), Molecular Cloning: A Laboratory Manual, Cold Spring Harbor Laboratories, New York; and Davis et al. (1986), Basic Methods in Molecular Biology, Elsevier. Particular methods include calcium phosphate co-precipitation (Graham et al. (1973), Virol. 52:456-467), direct micro-injection into cultured cells (Capecchi (1980), Cell 22:479-488), electroporation (Shigekawa et al. (1988), BioTechniques 6:742-751), liposome-mediated gene transfer (Mannino et al. (1988), BioTechniques 6:682-690), lipid-mediated transduction (Felgner et al. (1987), Proc. Natl. Acad. Sci. USA 84:7413-7417), and nucleic acid delivery using high-velocity microprojectiles (Klein et al. (1987), Nature 327:70-73).

The term "viral agent" as used herein refers to viruses (wild-type or genetically modified), viral particles, occlusion bodies, or the nucleic acids therefrom, as well as mixtures thereof.

The terms "isolated," "purified," or "biologically pure" as used herein, refer to material that is substantially or essentially free from components that normally accompany it as found in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In one exemplary embodiment, an isolated norovirus nucleic acid is separated from other nucleic acid sequences that flank it in its native state. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" or "nucleic acid sequence" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examplary analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

As used herein, the term "expression" or "express" or "expressed" as used herein, refers to the process by which a coding sequence of a gene is transcribed into a primary mRNA transcript, the primary mRNA transcript is processed into a mature mRNA, and the mature mRNA is translated into a protein. Expression can optionally include post-translation modifications of the resulting polypeptide The terms "polypeptide," "peptide" and "protein" are used interchangeably herein to refer to a polymer of amino acid residues. The terms apply to naturally occurring amino acid polymers and non-naturally amino acid polymers as well as amino acid polymers in which one or more amino acid residues is an artificial chemical mimetic of a corresponding naturally occurring amino acid.

The following terms are used to describe the sequence relationships between two or more nucleic acids or polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length norovirus genome sequence e.g., the C region of the major capsid protein of norovirus, or gene sequence given in a sequence listing.

The terms "identical" or percent "identity," in the context of two or more nucleic acids or polypeptide sequences, refer to two or more sequences or subsequences that are the same or have a specified percentage of nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

An exemplary algorithm for sequence comparason is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "promoter" or "promoter complex" or "promoter sequence" as used herein refers to an array of nucleic acid expression control sequences that direct transcription of a nucleic acid. As used herein, a "promoter" or "promoter complex" or "promoter sequence" comprises necessary nucleic acid sequences near the start site of transcription, such as, e.g., a polymerase II type promoter, a TATA element etc to "control" transcription of an operably linked nucleic acid. In some exemplary embodiments, a "promoter complex" or "promoter sequence" also includes distal enhancer or repressor elements, which can be, but are not necessarily located as much as several thousand base pairs from the start site of transcription. As is well known in the art, a "constitutive" promoter is a promoter that is active under most environmental and developmental conditions. An "inducible" promoter is a promoter that is active under environmental or developmental regulation, e.g., upregulation in response to wounding of plant tissues. Promoters may be derived in their entirety from a native gene, may comprise a segment or fragment of a native gene, or may be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. It is further understood that the same promoter may be differentially expressed in different tissues and/or differentially expressed under different conditions.

The expression "control transcription", "controlling transcription" or "control of transcription" or other grammatically equivalent phrases or expressions as used herein refers to the ability of an "expression control sequence" typically a promoter, to direct transcription of an operably linked nucleic acid sequence. In an exemplary embodiment, "controlling transcription" refers to initiating transcription. In another exemplary embodiment, "controlling transcription" refers to up-regulating transcription over a basal constitutive level of transcription.

The term "operably linked" refers to a functional linkage between a nucleic acid expression control sequence (such as e.g., a Bul409 promoter, or array of transcription factor binding sites) and a second nucleic acid sequence, wherein the expression control sequence directs expression e.g., transcription, of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression cassette" as used herein, refers to a nucleic acid construct, typically generated recombinantly or synthetically, which comprises a series of specified nucleic acid elements that permit transcription of a particular nucleic acid in a host cell. In an exemplary embodiment, an expression cassette comprises a heterologous nucleic acid to be transcribed, operably linked to a promoter.

Typically, an "expression cassette" is part of an "expression vector". The term "vector" as used herein, refers to nucleic acid capable of replicating in a selected host cell or organism. A vector can replicate as an autonomous structure, or alternatively can integrate into the host cell chromosomes and thus replicate along with the host cell genome. Thus, an "expression vector" is a nucleic acids capable of replicating in a selected host cell or organism e.g., a plasmid, virus, artificial chromosome, nucleic acid fragment, or any suitable construct known in the art, which comprises an "expression cassette".

I. Introduction:

I have now discovered a novel, spontaneously immortalized avian cell line, designated ZS-1, derived from primary chicken embryo fibroblasts (CEF). The ZS-1 cell line is free of endogenous retroviruses, including Avian Leukosis Viruses (ALV), and particularly ALV subgroup E. Moreover, the ZS-1 cell line is susceptible to (i.e., permits the growth of) all subgroups of ALV, including subgroup E. Cells of the ZS-1 cell line and sub-clones thereof may be used inter alia for the production of viral agents, including recombinant viral agents, expression of recombinant proteins, and diagnostic assays. Any viral agents or recombinant proteins produced using the ZS-1 cell line are free of contamination by endogenous virus or endogenous virus proteins.

Thus, the disclosure provides a novel immortal avian cell line which is free of endogenous retroviruses, including ALV subgroup E. Therefore, the disclosure provides a novel immortal avian cell line ZS-1 permits the growth of all subgroups of ALV, including subgroup E endogenous ALV which may be used for the production of viral agents, including ALV subgroup E. Furthermore, in exemplary embodiments, the novel immortal avian cell line, ZS-1, is used for the expression of recombinant proteins. In other exemplary embodiments, the novel immortal avian cell line ZS-1, is used for diagnostic assays to detect viral contamination of vaccines and other products.

II. Methods

A. General Methods

This invention utilizes routine techniques in the field of recombinant genetics. Basic texts disclosing the general methods of use in this invention include Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994)). Unless otherwise noted, technical terms are used according to conventional usage. Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

This disclosure also utilizes routine techniques in the field of cell and tissue culture. Basic texts disclosing the general methods of use in this invention include e.g., Waymouth, C., in: Cell Culture Methods for Molecular and Cell Biology, Vol. 11 Methods for Preparation of Media, Supplements, and Substratafor Serum-Free Animal Cell Culture, Barnes, D. W., et al., eds., New York: Alan R. Liss, Inc., pp. 23-68 (1984); Solomon, J. J., P. A. Long, and W. Okazaki (1971) Procedures for the in vitro assay of viruses and antibody of avian lymphoid leukosis and Marek's disease Agriculture Handbook #404, Agricultural Research Service, U.S. Department of Agriculture, U. S. Government Printing Office, Washington, D.C.; Merchant, D. J., 1%. H. Kahn, and W. H. Murphy (1964) Handbook of Cell and Organ Culture. Ed. 2. Burgess Publishing Co., Minneapolis, Minn.

III. Immortal Cell Line ZS-1

The spontaneously immortalized ZS-1 avian cell line was derived from primary Chicken Embryo Fibroblasts (CEF) which were obtained from a unique, endogenous virus-free line of chickens, designated 0.TVB*S1. This 0.TVB*S1 chicken line was itself developed at the United States Department of Agriculture, Agricultural Research Service (USDA-ARS) in East Lansing, Mich., as described by Zhang et al. (2008) (Development of an Endogenous Virus-Free line of Chickens Susceptible to All Subgroups of Avian Leukosis Virus. Avian Diseases. 52:412-418), the contents of which are incorporated by reference herein. The 0.TVB*S1 line was demonstrated free of endogenous virus, including all subgroups of ALV as described by Zhang et al (2008, supra).

In exemplary embodiments, cells of the ZS-1 cell line are used for the production of viral agents, including e.g., recombinant viral agents, expression of recombinant proteins, and diagnostic assays. Moreover, it is also understood that the production of viral agents, expression of recombinant proteins, and diagnostic assays may also be conducted using cultures or sub-clones of the immortalized ZS-1 cell line. Once cells of the ZS-1 cell line are in culture, it is possible to further sub-clone the cells to select for other physiological parameters that may vary in the cell population while still maintaining contact inhibition and susceptibility to virus infection. Any viral agents or recombinant proteins produced using the ZS-1 cell line or cultures or sub-clones thereof are free of contamination by endogenous virus or endogenous virus proteins.

Thus, in one exemplary embodiment, the ZS-1 cell line (or cultures or sub-clones thereof) are used for the production of viral agents. In some exemplary embodiments, production of viruses is accomplished using conventional in vitro cell culture techniques well known to those of skill in the art. Briefly, cells or clones of the ZS-1 cell line are provided (grown) in a culture medium in vitro, inoculated with the viral agent of interest, and incubated a sufficient time and under conditions effective to allow production of the viral agents. Following incubation, the viral agents so produced are harvested and recovered. The culture conditions, including cell density, multiplicity of infection (ratio of infectious virus particles to cells), time, temperature, media, etc. are not critical and may be readily determined by the practitioner skilled in the art. By way of example and without being limited thereto, cells of the ZS-1 cell line can be seeded into tissue culture flasks, roller bottles, stir culture, into hollow fiber reactors or other mass culture systems. For roller bottle virus propagation, the cells are seeded at about $2-5 \times 10^4$ cells/cm$^2$ of surface area. As the skilled practitioner will readily appreciate, methods for harvesting the virus after infection to obtain infectious virus may vary with particular viral agent. For instance, enveloped viruses egress into the culture media more slowly than non-enveloped virus. Stocks of virus can be obtained from the culture media alone or from cell lysates pooled with the conditioned media. For lytic viruses (those efficient at lysing a cell during virus egress), harvesting the conditioned culture media (e.g., spent media containing virus) after a gentle centrifugation step to remove cell debris is sufficient.

In another exemplary embodiment, the ZS-1 cell line (or cultures or sub-clones thereof) is used to express foreign proteins of commercial, medical, pharmaceutical, or veterinary importance by recombinant DNA techniques. These synthetic proteins may be produced by transforming cells of the ZS-1 cell line with a nucleic acid construct comprising a nucleic acid sequence encoding the protein of interest, operatively linked to one or more expression control sequences. The foreign protein is expressed upon culture of the transformed cells in vitro. The foreign protein of interest may be subsequently recovered or collected from the culture using conventional techniques.

A variety of vectors are suitable for use to prepare recombinant nucleic acid constructs, and are selected to be operable as cloning vectors or expression vectors in the ZS-1 cell line. Numerous vectors are known to practitioners skilled in the art, and selection of an appropriate vector is a matter of choice. The vectors may, for example, be bacteriophage, plasmids (including linearized or circular plasmids), viruses or hybrids thereof, such as those described in e.g., Maniatis et al. (1989) Molecular Cloning: A Laboratory Manual, Cold Springs Harbor Laboratory; or Ausubel et al. (1995) Current Protocols in Molecular Biology, John Wiley & Sons, Inc, the contents of each of which are herein incorporated by reference. Further, the vectors may be non-fusion vectors (i.e., those producing the proteins or peptides not fused to any heterologous polypeptide), or alternatively, fusion vectors (i.e., those producing the proteins fused to a vector encoded polypeptide). The fusion proteins would of course vary with the particular vector chosen. In accordance with a preferred embodiment, the vectors are eukaryotic expression vectors, particularly viruses. Exemplary viruses for use herein as vectors include e.g., retroviral vectors such as described by Foster et al. (supra), bacterial artificial chromosome (BAC) vectors described by Niikura et al. (J Gen Virol. 92:598-607. 2011), and BoHV-4 vectors described by Donofrio et al. (J Virol Methods. 148:303-306. 2008), the contents of each of which are incorporated by reference herein.

Regardless of the specific vector utilized, various sites may be selected for insertion of the isolated nucleotide sequences encoding the protein to be expressed. These sites are usually designated by the restriction enzyme or endonuclease that cuts them.

The particular site chosen for insertion of the selected nucleotide sequences into the vector to form a recombinant vector is determined by a variety of factors. These include size and structure of the protein or peptide to be expressed, susceptibility of the desired protein to enzymatic degradation by the host cell components and contamination by its proteins, expression characteristics such as the location of start and stop codons, and other factors recognized by those skilled in the art. None of these factors alone absolutely controls the choice of insertion site for a particular polypeptide. Rather, the site chosen reflects a balance of these factors, and not all sites may be equally effective for a given protein.

The nucleotide sequences comprising the protein encoding genes may be inserted into the desired vector by known techniques. If, however, the vector is to serve as an expression vector, the vector typically has a promoter effective for expression in the ZS-1 host cell, and the DNA sequences are inserted in the vector downstream of the promoter and operationally associated therewith (that is, the promoter should be recognized by the RNA polymerase of the host cell). In addition, the vector typically has a region which codes for a ribosome binding site positioned between the promoter and the site at which the DNA sequence is inserted so as to be operatively associated with the DNA sequence of the invention once inserted (in correct translational reading frame therewith). The vector is typically selected to provide a region which codes for a ribosomal binding site recognized by the ribosomes of the ZS-1 host cell into which the vector is to be inserted. The vector should contain a terminator with necessary 3' untranslated sequences for RNA termination, stability, and/or poly(A) tail addition (if eukaryotic). Alternatively, any or all of the above control sequences may be ligated to the coding sequence prior to insertion into the vector.

In accordance with yet another exemplary embodiment, the ZS-1 cell line (or cultures or sub-clones thereof) is used in diagnostic assays to detect the presence of viral agents in test samples. Without being limited thereto, the cell line is particularly suited for use in assays to detect viral contaminants in vaccines or recombinant proteins which have been produced using other techniques (i.e., not using the ZS-1 cell line) or in any animal, commercial or research product which may be susceptible to viral contamination. Viral contaminants are typically detected by a wide variety of known, conventional techniques, such as but not limited to, hemagglutination assays, antibody assays such as enzyme-linked immunosorbent assays (ELISA), direct sequencing of nucleic acids in a sample, using hybridization probes such as Southern blot analysis and polymerase chain reaction (PCR) amplification. However, false negative results may be generated in samples containing very low concentrations of a viral contaminant. Thus, in this embodiment, the cells of the ZS-1 cell line (or sub-clones thereof) are used to amplify or increase the concentration of viral contaminants by first inoculating the cells in an in vitro culture medium with the sample of interest and incubating for a sufficient time to allow any viral agents therein to replicate. Any replicated viral agents may then be detected using known or conventional techniques as described above. Moreover, in contrast with other CEF or immortalized CEF cell lines which are not susceptible to ALV of subgroup E, the ZS-1 cell line may be used in assays to determine if test samples have been contaminated with any subgroup of ALV, including subgroup E. A exemplary technique for the detection of any ALV in a sample which have been amplified by inoculation of cells of the ZS-1 cell line, is described e.g., by Silva et al. (2007) Avian Diseases. 51:663-667. 2007], the contents of which are incorporated by reference herein.

VI. Deposit Information

A deposit of the immortal cell line ZS-1, disclosed herein and recited in the appended claims has been made with the American Type Culture Collection (ATCC), Patent Depositary, 10801 University Blvd., Manassas, Va. 20110, U.S.A. The date of deposit was Sep. 24, 2014. All restrictions upon the deposit have been removed, and the deposit is intended to meet all of the requirements of 37 C.F.R. 1.801-1.809. The material description is: immortal cell line ZS-1 derived from primary Chicken Embryo Fibroblasts (CEF) from the virus free chicken line, 0.TVB*S1. The deposit will be maintained in the depository for a period of 30 years, or 5 years after the last request, or for the effective life of the patent, whichever is longer, and will be replaced as necessary during that period.

The following examples are offered to illustrate, but not to limit the invention.

EXAMPLES

Example 1

The following example illustrates isolation of the spontaneously immortalized ZS-1 avian cell line disclosed and claimed herein.

The spontaneously immortalized ZS-1 avian cell line was derived from primary CEF which were obtained from a unique, endogenous virus-free line of chickens, designated 0.TVB*S1. This 0.TVB*S1 chicken line was itself developed at the United States Department of Agriculture, Agricultural Research Service (USDA-ARS) in East Lansing, Mich., as described by Zhang et al. (Development of an Endogenous Virus-Free line of Chickens Susceptible to All Subgroups of Avian Leukosis Virus. Avian Diseases. 52:412-418. 2008), the contents of which are incorporated by reference herein. The 0.TVB*S1 line was demonstrated free of endogenous virus, including all subgroups of ALV as described by Zhang et al (2008, supra).

Primary CEF from the 0.TVB*S1 line were recovered from fertilized eggs of the 0.TVB*S1 by aseptically removing the embryonic torso of the 10-day-old embryos, mincing the tissue, dissociating the cells in trypsin-containing medium, and collecting and growing the dissociated cells in enriched culture medium. After incubation, cells of this primary culture were recovered by trypsinization, and plated in fresh culture medium containing 6% fetal calf serum for a second passage. Between the 10th and 25th passage, a working solution of Trypsin (0.25% Trypsin in PBS) was used to briefly loosen and then to discard some of the senescent (aging) cells from the surface of the petri dish before completely dissociating the cells in the petri dish by trypinization to passage the cells. After repeated passage, spontaneously immortalized cells were obtained from the mixed cell population in pure form. These cells were recovered and designated ZS-1. Cells of the ZS-1 cell line are immortal and have been passaged over 40 passages, remaining stable, morphologically uniform and similar with the original CEF of 0.TVB*S1. The genotype of the ZS-1 cells is the same as that described for the 0.TVB*S1 line by Zhang et al. (2008, supra). Genomic analysis using the techniques described in Zhang et al. (2008, supra) has confirmed that the ZS-1 cell line is homozygous TVB*S1 allele and free of endogenous virus (ev) genes. Significantly, as determined by Southern blot analysis, the genome of the ZS-1 cell line does not possess any of the more than 20 known ALV subgroup E ev genes which encode for endogenous viruses or their components, and which genes are present in virtually all chicken genomes.

In contrast with the DF-1 cell line described by Foster et al. the ZS-1 cell line described herein is not only free of endogenous ALV, but is susceptible to all subgroups of ALV: A, B, C, D, and J, as well as subgroup E. The ZS-1 cell line is also susceptible to other retroviruses and Marek's Disease Virus (MDV). Cells of the ZS-1 cell line possess receptors for all subgroups of ALV, permitting the growth of all ALV subgroups, including any subgroup E ALV, while the DF-1 cell line does not. Therefore, the ZS-1 cell line can be used not only to produce subgroup E ALV, but it may be used in assays to determine if test samples have been contaminated with subgroup E ALV.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An immortal cell line ZS-1 having Accession Number ATTC PTA-121623, wherein the cell line ZS-1 is derived from primary Chicken Embryo Fibroblasts (CEF) from the virus free chicken line, 0.TVB*S1, wherein the immortal cell line ZS-1 is free of avian leukosis virus (ALV) and supports virus replication.

2. A cell culture or sub-clone of the immortal cell line ZS-1 of claim 1.

3. The cell culture of claim 2, wherein cells comprising the cell culture are transformed with a heterologous nucleic acid construct operably linked to one or more expression control sequences.

4. A method for growing a virus comprising:
   (i) inoculating cells of the immortal cell line ZS-1 of claim 1 with a virus;
   (ii) allowing the virus to replicate in the cells of the inoculated immortal cell line ZS-1 thereby producing replicated virus; and
   (iii) recovering the replicated virus.

5. The method of claim 4 wherein the virus is a retrovirus.

6. The method of claim 5 wherein the retrovirus is an Avian Leukosis Virus.

7. The method of claim 6 wherein the Avian Leukosis Virus is an Avian Leukosis Virus subgroup E.

8. The method of claim 4, wherein the method is used to test for the presence of viruses comprising inoculating the cell culture or sub-clone of immortal cell line ZS-1 in step (i) with a test sample.

9. A method for producing a recombinant protein comprising:
   (i) transforming cells of the immortal cell line ZS-1 of claim 1 with an expression vector comprising a nucleic acid sequence that encodes the recombinant protein operatively linked to a promoter effective for expression in the cells of the immortal cell line ZS-1, thereby providing transformed cells;
   (ii) allowing the transformed cells to express the recombinant protein; and
   (iii) recovering the recombinant protein from the transformed cells.

* * * * *